United States Patent [19]

Bogdanovic et al.

[11] Patent Number: 5,215,710

[45] Date of Patent: Jun. 1, 1993

[54] INTERMETALLIC COMPOUNDS

[75] Inventors: Borislav Bogdanović; Ursula Wilczok, both of Mülheim/Ruhr, Fed. Rep. of Germany

[73] Assignee: Studiengesellschaft Kohle M.b.H., Mulheim, Fed. Rep. of Germany

[21] Appl. No.: 857,362

[22] Filed: Mar. 25, 1992

Related U.S. Application Data

[60] Division of Ser. No. 547,430, Jul. 2, 1990, Pat. No. 5,133,920, which is a continuation of Ser. No. 304,994, Feb. 1, 1989, abandoned, which is a division of Ser. No. 39,495, Apr. 16, 1987, Pat. No. 4,828,606.

Foreign Application Priority Data

Apr. 22, 1986 [DE] Fed. Rep. of Germany ....... 3613532

[51] Int. Cl.$^5$ .................. C22C 19/00; C22C 23/00; C22C 24/00; C22C 5/04
[52] U.S. Cl. .................. 420/400; 420/402; 420/441; 420/463; 420/466; 420/415; 148/304
[58] Field of Search ............. 420/402, 463, 441, 466, 420/400, 415; 148/420, 403

[56] References Cited

U.S. PATENT DOCUMENTS

| | | | |
|---|---|---|---|
| 3,615,270 | 10/1971 | Snover | 23/360 |
| 4,446,101 | 5/1984 | Bernauer et al. | 420/424 |
| 4,554,152 | 11/1985 | Bogdanovic | 423/647 |

FOREIGN PATENT DOCUMENTS

| | | | |
|---|---|---|---|
| 1448362 | 6/1966 | France | |
| 55-149101 | 11/1980 | Japan | 420/441 |
| 46468 | 1/1963 | Poland | 420/441 |

OTHER PUBLICATIONS

Shunk "Constitution of Binary Alloys" Materials Science and Engineering Series, second supplement 1969, p. 492.

Jones, Deborah et al., "Intermetallic Phases in the Mg-Pd System: X-ray Absorption Spectroscopic Characterization of the Amorphous Mg-Pd-C-H Alloy", Chem. Material 4(3), 620-S, 1992.

Bogdanovic, Noreus, et al. "Structural Analysis of a Novel C-Stabilized Mg-Pd-Alloy", Journal Less—Common Metal, 169(2), 369-73 1991.

Bogdanovic et al., "A New Pathway to Mg$_2$Ni and Mg-Ni Carbide", Journal of Less-Common Metals, 131 (1987) pp. 163-173.

103:108661a, Shen et al., "Chemical synthesis of hydrogen-storing alloys". Chem. Ab., V. 103, (Oct. 1985), p. 254.

84:11167v, Bronger et al., "Synthesis and structure of lithium-platinum ... ", Chem. Ab. V. 94 (1976) p. 432.

Primary Examiner—Deborah Yee
Attorney, Agent, or Firm—Sprung Horn Kramer & Woods

[57] ABSTRACT

Intermetallic compounds and hydrides thereof, characterized in that they have been prepared by reacting hydrides of the elements of the main groups I, II, III and IV of the Periodic Table, magnesium hydridehalides or magnesium dialkyls having the general formula MgR$_2$ (R=alkyl) in a solvent with bisallyl metal compounds of the metals of the subgroup VIII of the Periodic Table or of zinc or with the homologues of the bisallyl compounds of said metals, and processes for preparing said compounds.

12 Claims, 1 Drawing Sheet

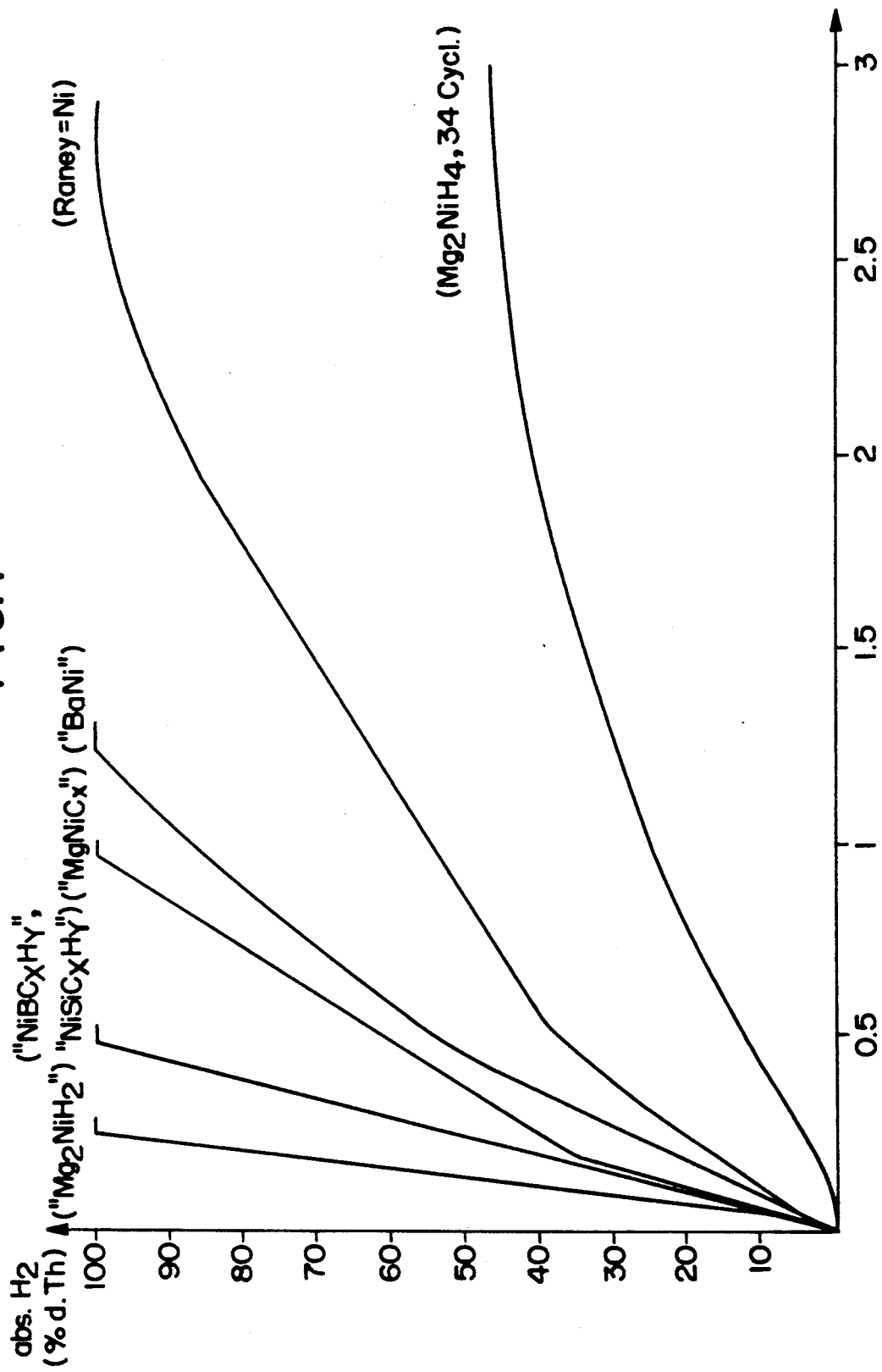

INTERMETALLIC COMPOUNDS

This is a division of application Ser. No. 547,403, filed Jul. 2, 1990 now U.S. Pat. No. 5,133,920 which is a continuation of Ser. No. 304,994, filed Feb. 1, 1989, now abandoned, which is a division of Ser. No. 39,495, filed Apr. 16, 1987, now U.S. Pat. No. 4,828,606.

The present invention relates to a process for preparing intermetallic compounds or the hydrides thereof by means of a non-metallurgical, i.e. wet-chemical, route under extremely mild conditions (e.g. room temperature, normal pressure), whereby the products are obtained in a finely distributed, highly active predominantly amorphous state.

Intermetallic compounds and the hydrides thereof have gained increasing technical importance during the recent 10 to 15 years.

According to prior art, such intermetallic compounds or metal alloys are prepared from two or more components by a melt process at a high temperature (cf. H. Buchner, "Energiespeicherung in Metyllhydriden", Springer Verlag 1982, page 65).

Furthermore, evaporation techniques of metals such as, e.g., the preparation of the supra-conducting $Nb_3Si$ (E. Amberger, U. Siefken, J. Less-Common Metals 75, (1980) 273) have become known.

Inter-metal compounds of metals of the main groups V and VI of the Periodic Table, on the one hand, with metals of the groups II to IV, on the other hand, such as GaAs., CdSe, SnSe which—such as, e.g., GaAs—are used in semiconductor technology, can be prepared by a "non-metallurigcal route" by the reaction of organometal compounds of the respective metals [$Ga(CH_3)_3$), $Al(CH_3)_3$)] with element hydrides ($PH_3$, $AsH_3$) in the gaseous state at high temperatures (of from 500° C. to 700° C.). The method has gained technical relevance for the preparation of semiconductor material (P. D. Dapkus, "Metalorganic chemical vapor deposition", Annual Review Material Sciences 12 (1982) 243].

L. H. Dubois and R. G. Nuzzo (U.S. Pat. No. 4,507,401) claim a process for preparing intermetallic compounds used as catalysts for dehydrogenations of alkanes, which process is characterized in that metals, such as, e.g., finely distributed metallic nickel, fixed to inorganic carriers are reacted with gaseous organometal compounds or metal hydrides, such as, e.g., hexamethyldisilane or $Si_2H_6$, at elevated temperature (e.g. 300° C.). Evidence of the formation of intermetallic compounds, e.g. of nickel silicides in the reaction of Ni with $Si_2H_6$, has not been furnished.

Intermetallic compounds in amorphous form ("metallic glasses") are commercially produced by quenching melts, in which processes extremely high cooling rates ($10^{6°}$ C./s) are necessary to eliminate any formation of crystallization seeds, which involves high technical expenditure (P. Duwez, Progr. Solid State Chem. 3 (1966) 377]. In addition, intermetallic compounds in an amorphous state may be obtained by the condensation of metal vapors [W. Buckel, R. Hilsch, Z. Physik 138 (1954) 109] or by the diffusion of the metals at temperatures below the crystallization temperature [$Au_{1-x}La_x$ ($0,3 \leq x \leq 0,5$), R. B. Schwarz, W. L. Johnson, Phys. Rev. Lett. 51 (1983) 415].

Ternary hydrides (hydrides of intermetallic binary compounds) have been known to be prepared by subjecting intermetallic compounds, after a so-called activation process (comminution, full heating under a protective gas), to a series of from 5 to 15 hydrogenation-dehydrogenation cycles until the optimum hydrogenation rate and load will have been reached.

Further methods of the preparation of hydrides of intermetallic compounds comprise the reaction of metal hydrides with metals in the presence of hydrogen at high temperatures [e.g. $Eu_2RuH_6$, J. S. Thompson et al., Inorg. Chem. 14 (1975) 1866; $Yb_2RhH_6$, R. Lindsay et al., Inorg. Chem. 15 (1976) 3050] or the reaction of two metals in a finely distributed state with hydrogen at high temperatures [$Mg_2FeK_6$, J.-J. Didisheim et al., Inorg. Chem. 23 (1984) 1953; $Mg_2CoH_5$, P. Zolliker et al., Inorg. Chem. 24 (1985) 4177].

Intermetallic hydrides in an amorphous state are obtainable by the hydrogenation of crystalline intermetallic compounds at a temperature below the crystallization temperature of the hydrides [hydrogenation of $LaNi_2$, $LaNi_3$ and $La_2Ni_7$: H. Oesterreicher, J. Clinton, H. Bittner, Nat. Res. Bull. 11 (1976) 1241; hydrogenation of $Zr_3Rh$: K. Samwer, X. L. Yeh, W. H. Johnson, J. Non-Crystalline Solids 61, 62 (1984) 631].

It has now surprisingly been found that intermetallic compounds or the hydrides thereof may be readily formed from the hydrides of the elements of the main groups I to IV of the Periodic Table ($M^1H_n$ component), e.g. HMgCl, or magnesium dialkyls in an organic solvent at a temperature of from −100° C. to 100° C.—and preferably at from 0° C. to +50° C.—by the reaction with bisallyl metal compounds of the metals Ni, Pd, Pt or Zn [$M^2(C_3H_5)_2$ component), for example, allyl or homologues thereof such as methallyl, e.g. bis($3$-methallyl) nickel or -palladium. As suitable metal hydrides there are preferred to be employed magnesium hydride (European Patent No. 0 003 564) and lithium hydride (U.S. Pat. No. 4,396,589). Characteristic for the reaction according to the invention is the partial or complete removal of the allyl group of the $M^2(C_3H_5)_2$ component in the form of propane (equations 1 to 4 hereinbelow) and the precipitation of the intermetallic compounds or of the hydrides thereof in an amorphous state.

Accordingly, the present invention relates to intermetallic compounds and the hydrides thereof which are characterized by that they have been prepared by reacting hydrides of the elements of the main groups I, II, III and IV of the Periodic Table, magnesium hydridehalides or magnesium dialkyls having the general formula $MgR_2$ (R=alkyl) in a solvent with bisallyl metal compounds of the metals of the subgroup VIII of the Periodic Table or of zinc, the bisallyl compound including allyl and homologues thereof.

The invention further relates to a process for the preparation of intermetallic compounds and of the hydrides thereof, which process is characterized in that hydrides of elements of the main groups I, II, III and IV of the Periodic Table, magnesium hydridehalides or magnesium dialkyls having the general formula $MgR_2$ (R=alkyl) are reacted in a solvent with bisallyl metal compounds of the metals of the subgroup VIII of the Periodic Table or of zinc.

The hydrides of the elements of the main groups I and II of the Periodic Table are preferred in the present invention.

The elements of the groups I to IV of the Periodic Table may be exemplified by lithium, sodium, potassium, beryllium, magnesium, calcium, strontium, barium, boron, and silicon. Among these, lithium, magnesium, calcium, barium, boron and silicon are preferred. Magnesium is most preferred.

As the magnesium hydridehalide there may be used magnesium chloridehydride and magnesium bromidehydride, magnesium chloridehydride being preferred.

In the general formula $MgR_2$ of the magnesium dialkyls, the alkyl moieties R preferably have from 1 to 8 carbon atoms.

As metals of the subgroup VIII of the Periodic Table there may be mentioned preferably nickel, palladium or platinum. However, the other metals of the subgroup VIII of the Periodic Table, viz, iron, cobalt, nickel, ruthenium, rhodium, osmium and iridium may be employed as well.

The solvents to be employed in the present invention may be any solvents which are inert to the reactants. Preferred solvents are tetrahydrofuran, toluene and ether.

The reaction may be carried out at conventional temperatures within the range of from $-100°$ C. to $+100°$ C., and preferably of from $0°$ C. to $+50°$ C.

As examples of intermetallic compounds and of the hydrides thereof according to the present invention there may be mentioned the following:

Intermetallic compound MgPd in the amorphous state;
Intermetallic compound MgNi in the amorphous and in the crystalline states;
Crystalline, intermetallic compound $Mg_2Pd$ and its hydride $Mg_2PdH_2$ in the amorphous and in the crystalline states;
Intermetallic compound $Mg_2Pt$ and its hydride $Mg_2PtH_2$;
Intermetallic compound MgPt;
Intermetallic compounds $Li_2Ni$ and LiNi;
Intermetallic compounds BaNi and $Ba_2Ni$;
Intermetallic compound LiPd in the amorphous state;
Intermetallic compound $Li_2Pt$ in the amorphous state; and
Intermetallic compound $Ca_2Pd$ and its hydride.

The formation of the intermetallic compounds (equations 1, 1a, 3a and 4) and of the hydrides thereof (equations 2, 3) in the process according to the invention may be illustrated by the following reaction equations:

$$2/n\ M^1H_n + M^2(C_3H_5)_2 \longrightarrow M^1{}_{2/n}M^2 + 2\ C_3H_6 \quad (1)$$

| $M^1$ | n | $M^2$ | Example |
|-------|---|-------|---------|
| Mg | 2 | Ni | 3 |
| Mg | 2 | Pd | 7 |
| Mg | 2 | Pt | 9 |
| Ba | 2 | Ni | 13 |
| Li | 1 | Ni | 14 |
| Li | 1 | Pt | 17 |

$2\ MgClH + Ni(\eta^3\text{-}C_3H_5)_2 \longrightarrow MgNi\ \downarrow\ +$
$MgCl_2\ (\text{soln.}) + 2\ C_3H_6$ (1a)

(Example 4)

$2\ M^1H_2 + M^2(C_3H_5)_2 \longrightarrow M^1{}_2M^2H_2\ \downarrow\ + 2\ C_3H_6$ (2)

| $M^1$ | $M^2$ | Example |
|-------|-------|---------|
| Mg | Ni | 1 |
| Mg | Pd | 6 |
| Mg | Pt | 8 |
| Ca | Pd | 11 |

| Ba | Ni | 12 |

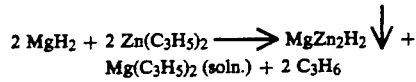

$2\ MgH_2 + 2\ Zn(C_3H_5)_2 \longrightarrow MgZn_2H_2\ \downarrow\ +$
$Mg(C_3H_5)_2\ (\text{soln.}) + 2\ C_3H_6$ (3)

(Example 10)

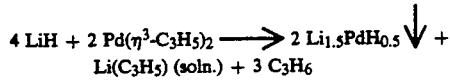

$4\ LiH + 2\ Pd(\eta^3\text{-}C_3H_5)_2 \longrightarrow 2\ Li_{1.5}PdH_{0.5}\ \downarrow\ +$
$Li(C_3H_5)\ (\text{soln.}) + 3\ C_3H_6$ (3a)

(Example 16)

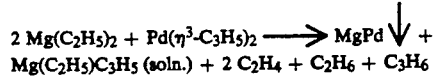

$2\ Mg(C_2H_5)_2 + Pd(\eta^3\text{-}C_3H_5)_2 \longrightarrow MgPd\ \downarrow\ +$
$Mg(C_2H_5)C_3H_5\ (\text{soln.}) + 2\ C_2H_4 + C_2H_6 + C_3H_6$ (4)

(Example 23)

The process according to the present invention allows an easy preparation of intermetallic compounds so far unknown as well as of previously known intermetallic compounds or previously known ternary hydrides in an amorphous and particularly reactive state and also in the crystalline state. The intermetallic compounds or hydrides thereof as primarily obtained in an amorphous state according to the equations 1 to 4 may be rid of contaminations (organic components) by repeated hydrogenation-dehydrogenation cycles.

Upon variation of the molar ratio of the two reactants $M^1H_n$ and $M^2(C_3H_5)_2$ there will be obtained various intermetallic compounds or hydrides thereof, some of which are so far unknown, as will be further illustrated by way of Examples.

In the Mg-Ni phase diagram there have so far been known two intermetallic phases, $Mg_2Ni$ and $MgNi_2$, which are obtainable by melt processes. The intermetallic compound $Mg_2Ni$ may be reversibly hydrogenated to form the intermetallic compound $Mg_2NiH_4$ which is one of the best known high-temperature hydrogen storage systems; contrary thereto, the intermetallic compound $MgNi_2$ is not capable of being hydrogenated [J. J. Reilly, R. H. Wiswall, Inorg. Chem. 7 (1968) 2254].

In the reaction of catalytically prepared magnesium hydride with bis($n^3$-allyl)nickel in a molar ratio of 2:1 the present process yields an amorphous hydride of the approximate composition $Mg_2NiH_2$.

In contrast to the metallurgically prepared $Mg_2Ni$, the product prepared according to the invention (specific surface area 20 m²/g) may be reversibly hydrogenated already under normal pressure at 200° C. to form $Mg_2NiH_4$.

If, however, catalytically prepared magnesium hydride is reacted with bis($\eta^3$-allyl)nickel in a molar ratio of 1:1 (equation 1) or soluble magnesium chloridehydride is reacted with bis($\eta^3$-allyl)nickel in a molar ratio of 2:1 (equation 1a), then in both cases an amorphous solid is obtained which has been proven to be a so far unknown intermetallic compound having the composition of MgNi. MgNi cannot be hydrogenated under standard conditions. MgNi is a metastable compound which is not accessible via the metallurgical route. Only upon continued annealing at 730° C. MgNi is slowly and incompletely converted into the known thermodynamically stable $Mg_2Ni$.

In the reaction of catalytically prepared magnesium hydride with bis($\eta^3$-allyl)palladium or bis($\eta^3$-methallyl)palladium in a molar ratio of 2:1 there is formed a so far unknown amorphous hydride $Mg_2PdH$ which upon dehydrogenation and a hydrogenation/dehydrogenation cycle is converted into a previously unknown crystalline intermetallic compound $Mg_2Pd$.

Active magnesium hydride reacts with bis($\eta^3$-allyl)-palladium according to equation 1 in a molar ratio of 1:1 to form the amorphous intermetallic compound mgPd which may also be obtained from magnesium diethyl and bis($\eta^3$-allyl)palladium in a molar ratio of 2:1 (equation 4). An intermetallic compound MgPd in an amorphous state has so far not been known, in contrast to the known crystalline cubic MgPd (CsCl type) [S. N. Sharma, A. Weiss, J. Less-Common Metals 104 (1984) 45] and the known crystalline tetragonal $Pd_{1.1}Mg_{0.9}$ (AuCu type) [L. Westin, Acta Chem, Scand. 22 (1968) 2574].

Catalytically prepared magnesium hydride reacts with bis($\eta^3$-allyl)platinum in a molar ratio of 2:1 to form the amorphous ternary hydride $Mg_2PtH_2$ (equation 2) and in a molar ratio of 1:1 to form the intermetallic compound MgPt (equation 1).

Active lithium hydride (U.S. Pat. No. 4,396,589) reacts with bis($\eta^3$-allyl)nickel in a molar ratio of 2:1 to form the amorphous $Li_2Ni$ (equation 1) and in a molar ratio of 1:1 to form amorphous LiNi.

In the system nickel-lithium so far no intermetallic phases have been determined [Y. Takeuchi et al., Metallwissenschaft und Technik 20, January 1966, 2]. Thus, for example, nickel is capable of dissolving only 0.4% of lithium at 1200° C., while a lithium melt at the name temperature is capable of dissolving only 3.5% of nickel. The process according to the invention makes it possible to prepare amorphous lithium-nickel intermetallic compounds.

Barium hydride reacts with bis($\eta^3$-allyl)nickel in a molar ratio of 2:1 to form the amorphous ternary hydride $Ba_2NiH_2$ (equation 2) and in a molar ratio of 1:1 to form the previously unknown amorphous intermetallic compound BaNi (equation 1).

In the system nickel-barium [Y. Takeuchi et al.] so far no intermetallic phases have been determined. The two alloy components are only partially miscible in the liquid state and form a miscibility gap in a wide concentration range. In accordance with the process of the invention it has now become possible to prepare amorphous nickel-barium intermetallic compounds and ternary hydrides, respectively.

The present process further enables preparing the known or unknown compounds set forth hereinbelow and/or hydrides thereof, respectively, in addition to the aforementioned compounds.

Active magnesium hydride reacts with bis(allyl) zinc in a molar ratio of 1:1 to form the so far unknown amorphous hydride $MgZn_2H_2$ (equation 3).

Catalytically prepared lithium hydride reacts with bis($\eta^3$-allyl)palladium in a molar ratio of 2:1 (equation 3a) to form an amorphous intermetallic compound having the composition $Li_{1.5}Pd$.

In the reaction of active lithium hydride with bis($\eta^3$-allyl)platinum in a molar ratio of 2:1 (equation 1) there is formed an amorphous intermetallic compound having the composition $Li_2Pt$ which is capable of being reversibly hydrogenated under standard conditions.

The reaction of calcium hydride with bis($\eta^3$-allyl)palladium in a molar ratio of 2:1 (equation 2) results in the hydrogenation of the Palladium present in the product mixture.

In summary, the following advantages over the state of the art of the present process for preparing intermetallic compounds and/or the respective hydrides may be mentioned:

1. The preparation is carried out via a wet-chemical route under extremely mild conditions (e.g. room temperature) and, thus, enables the preparation of compounds of this type to be effected which are not obtainable via a metallurgical route as they do not exist at high temperatures (being metastable). Those new intermetallic compounds, once prepared at a low temperature, such as, for example, MgNi, may prove to be of a surprising thermal stability.

2. By varying the molar ratio of the starting components $M^1H_n$ and $M^2(C_3H_5)_2$ in the synthesis, various defined intermetallic compounds or the hydrides thereof aimed at may be prepared.

3. Due to the mile reaction conditions, the intermetallic compounds or the hydrides thereof are obtained in an extremely finely distributed highly reactive form, i.e. such having a large specific surface area. This gives rise, on the one hand, to superior kinetics of hydrogenation-dehydrogenation as compared to that of the metallurgically prepared intermetallic compounds and, on the other hand, to an increased catalytic activity of said compounds.

Intermetallic compounds and/or the hydrides thereof obtained according to the present process are mostly amorphous, i.e. in the form of metallic glasses, since they have been produced at temperatures below the crystallization temperature.

Thus, the process is a novel process for preparing amorphous metallic materials and the hydrides thereof wherein the conventional techniques of extreme quenching are dispensable. As a rule, said compounds may be converted into crystalline intermetallic compounds by heating or annealing at temperatures above the crystallization temperature.

The intermetallic compounds or hydrides thereof preparable according to the process of the present invention may be used, inter alia, as reversible hydrogen storage systems, as catalysts, as regeneratable hydrogen donors and acceptors for chemical processed and further for hydrogen separation and purification.

Among the physicochemical properties of certain intermetallic compounds and alloys of particular technical interest is the superconductivity below relatively high superconductive transition temperatures $T_c$ (transition from the metallic state to the superconductive). The highest superconductive transition temperature of all superconductors so far known is that of $Nb_3Ga$ amounting to 23.2 K. Superconducting intermetallic compounds such as, e.g., $Nb_3Sn$, are technically used as superconducting materials in cryomagnets for producing extremely high magnetic fields (>2 Tesla).

A further application in the field of intermetallic compounds is the "metallic glasses", i.e. the intermetallic compounds or alloys in an amorphous state. Technical applications of magnetic glasses, due to their magnetic properties, are contemplated to exist in transformer technology (energy saving in power transformation due to use of metallic glasses as transformer cores) and in application as metallic materials having a particularly high mechanical strength and/or corrosion resistance. Metallic glasses are also of interest with view to the properties thereof as superconductors and as catalysts.

The invention will be further described in the following Examples in conjunction with the accompanying drawing, wherein FIG. 1 is a plot of the hydrogen consumption rate against the reaction time for various nickel catalysts.

All operations described in the following Examples are carried out under argon.

EXAMPLE 1

6.81 g of $MgH_2$ (223 mmol) (composition: Mg 84.7, H 7.0, C 4.6, Cl 2.6, Cr 0.4%; 86 per cent after thermolysis) [European Patent No. 0 003 564] were suspended in 200 ml of tetrahydrofuran (THF) and were admixed in a closed system with a solution of 15.76 g (112 mmol) of $Ni(\eta^3-C_3H_5)_2$ in 50 ml of THF. The suspension was stirred at room temperature (RT), whereupon the initial yellow-orange color of the suspension changed to black within 0.5 h. After 36 h the Ni concentration in the solution remained constant at 0.07 mmol of Ni/ml; after 96 h, $Ni(\eta^3-C_3H_5)_2$ was no longer detectable in the solution. The batch was stirred at RT for 96 h altogether; then the volatile components were evaporated at RT and 0.27 mbar (0.2 mmHg) and condensed in two cold traps arranged in series ($-78°$ and $-196°$ C.). The gases condensed in the trap cooled at $-196°$ C. were evaporated, collected in a gas burette and analyzed by mass spectroscopy; the condensate of the trap cooled at $-78°$ C. was analyzed for diallyl and residual gases by gas chromatography. Thus, of the $C_3M_5$ groups employed as $Ni(\eta^3-C_3H_5)_2$, 76% were detected in the form of propane and 3% were detected in the form of propane. The solid residue was stirred with fresh THF (500 ml) for 24 h, the black solid was separated from the solution by filtration, washed with THF until colorless and then with pentane and thereafter dried at RT under high vacuum.

Obtained were 13.70 g of a black, highly pyrophoric powder having the composition Mg 15.9, Ni 40.3, H 3.9, C 15.2, Cl 0.4, and Cr 0.04% (83% of the theory, relative to Ni), conforming to an empirical formula of $Mg_{2.15}Ni_{1.00}H_{5.68}C_{1.83}Cl_{0.02}$ and having a specific surface area of 98 m²/g (BET method). According to the X-ray powder analysis, the solid was amorphous, except for very weak lines of $MgH_2$.

In a fully automatically operated, electronically controlled apparatus 11.30 g of the above powder were first heated to 400° C. and subjected to a series of 34 hydrogenation/dehydrogenation cycles.

Upon rapid heating (about 40° C./min), an exothermic gas evolution began at 120° C. (internal temperature of the sample) in the course of which the sample was heated to 300° C. for a short time, and 1200 ml of gas (20° C., 1 bar) having the composition $H_2$ 65%, $CH_4$ 5%, $C_3H_8$ 8%, n—$C_4H_{10}$ 11%, n—$C_4H_8$ 5% were released. From 270° C. to 335° C. (internal temperature of the sample) there was an endothermic evolution of gas within 15 min whereby 1380 ml of gas (20° C., 1 bar) having the composition $H_2$ 71%, $CH_4$ 17%, $C_3H_8$ 2%, n—$C_4H_8$ 8% were evolved. In the subsequent hydrogenation/dehydrogenation cycles the samples with respect to kinetics showed a behaviour comparable to that of a sample of metallurgically prepared $Mg_2Ni$ [J. J. Reilly, R. H. Wiswall, Inorg. Chem, 7 (1968) 2254]. After the first 5 cycles (hydrogenation: 334° C., 15 bar, 1.5 h; dehydrogenation: 334° C., normal pressure, 1.5 h), the $H_2$ capacity of the sample in the residual 29 cycles (hydrogenation: 200° C. and 260° C., 1, 3, 5 and 10 bar, 1 h; dehydrogenation: 334° C., normal pressure, 1.5 h) remained constant at 2.65% by weight (calc. for $Mg_2NiH_4$ 3.62% by weight). In contrast to the metallurgical $Mg_2Ni$ sample, the $Mg_2Ni$ thus prepared was capable of being hydrogenated under normal pressure at 200° C., while in its X-ray powder diagram it was identical with the metallurgical $Mg_2Ni$ sample.

After another hydrogenation, there was obtained a carbon free $Mg_2NiH_4$ (composition: Mg 42.9, Ni 48.6, H 2.64, Cl 1.6, and Cr 0.2%) which was identified as such by X-ray powder analysis [Z. Gavra et al., Inorg. Chem. 18 (1979) 3595].

EXAMPLES 2 TO 10

The experiments in Examples 2 to 10 were carried out analogously to Example 1. The starting materials, reaction conditions and experimental results are summarized in Tables 1 and 1a.

TABLE 1

Reactions of catalytically prepared magnesium hydride with bis(allyl)metal compounds ($M^2A_2$) at room temperature to give intermetallic compounds or ternary hydrides.

| Example No. | $MgH_2$[a] g (mmol) | $M^2A_2$ g (mmol) | Solvent [ml] | React. Time [h] | Propene[b] [%] | Solid [g] | Comp.: Elem. Analysis [%] Mg M H C Cl Empirical Formula | Yield[c] [%] | RP[d] |
|---|---|---|---|---|---|---|---|---|---|
| 2 | 1.02 (33.7) | Ni(meth.-A)$_2$[e] 2.60 (16.8) | THF (35) | 192[f] | 79.4 (0.6) | 1.25 | 44.3 35.0 4.0 9.5 $Mg_{3.05}Ni_{1.00}H_{8.02}C_{1.33}$ | 44 | amorphous |
| 3 | 1.18 (35.2) | NiA$_2$ (35.2) | THF (50) | 116[g] | 68 (2) | 3.39 | 22.7 54.3 3.2 17.1 $Mg_{1.00}Ni_{1.00}H_{3.41}C_{1.52}$ | 89 | amorphous |
| 4 | 4.83 (80.0)[h] | NiA$_2$ (40.0) | THF (123) | 48 | 73 (3) | 2.02 | 20.5 51.5 2.0 13.2 7.5 $Mg_{0.96}Ni_{1.00}H_{4.33}C_{1.25}Cl_{0.25}$ | 44 | amorphous |
| 5 | 1.33 (43.3) | PdA$_2$ 4.04 (21.5) | THF (55) | 17[i] | 96 | 3.50 | 28.3 66.6 1.66 3.2 $Mg_{1.86}Pd_{1.00}H_{2.63}C_{0.43}$ | 99 | amorphous |
| 6 | 0.79 (23.5) | Pd(meth.-A)$_2$[j] 2.63 (12.1) | Tol. (40) | 96[k] | 78 (4) | 2.08 | 28.5 62.2 2.18 6.9 $Mg_{2.01}Pd_{1.00}H_{3.7}C_{1.00}$ | 99 | |
| 7 | 0.55 (17.8) | PdA$_2$ 3.26 (17.3) | THF (65) | 24[i] | 93 | 2.38 | 16.5 73.2 1.31 4.4 $Mg_{0.98}Pd_{1.00}H_{1.89}C_{0.53}$ | 95 | amorphous |
| 8 | 1.14 (37.0) | PtA$_2$ 4.91 (17.7) | THF (76) | 20[i] | 95 (7) | 4.43 | 18.7 74.7 0.97 4.3 $Mg_{2.00}Pt_{1.00}H_{2.51}C_{0.93}$ | 96 | amorphous |
| 9 | 0.45 (14.6) | PtA$_2$ 4.04 (14.6) | THF (45) | 24[i] | 81 (7) | 2.87 | 10.7 84.8 0.65 3.74 $Mg_{1.02}Pt_{1.00}H_{1.48}C_{0.72}$ | 86 | amorphous |
| 10 | 0.71 (23.1) | ZnA$_2$ | THF | 20 | 46 | 1.55[l] | 14.6 79.1 0.89 0.98 | 82 | Zn |

TABLE 1-continued

Reactions of catalytically prepared magnesium hydride with bis(allyl)metal compounds ($M^2A_2$) at room temperature to give intermetallic compounds or ternary hydrides.

| Example No. | $MgH_2^{a)}$ g (mmol) | $M^2A_2$ g (mmol) | Solvent [ml] | React.-Time [h] | Propene$^{b)}$ [%] | Solid [g] | Comp.: Elem. Analysis [%] Mg M H C Cl Empirical Formula | Yield$^{c)}$ [%] | RP$^{d)}$ |
|---|---|---|---|---|---|---|---|---|---|
| | | 3.37 (22.9) | (60) | | (2) | | $Mg_{1.00}Zn_{2.00}H_{1.47}C_{0.14}$ | | |

$^{a)}MgH_2$ 85%, prepared.
$^{b)}$The figures in brackets denote % of propane.
$^{c)}$Relative to initially employed M.
$^{d)}$X-ray powder analysis.
$^{e)}Bis(\eta^3$-methallyl)nickel.
$^{f)}$53% of $bis(\eta^3$-methallyl)nickel unreacted after 48 h; after 8 d only traces pf $bis(\eta^3$-methallyl)nickel detected in the solution.
$^{g)}C_3H_6$: 60% of theory after 48 h; after further 88 h $bis(\eta^3$-allyl)nickel no longer detectable in solution.
$^{h)}$HMgCl used in the place of $MgH_2$.
$^{i)}$After this time any $bis(\eta^3$-allyl)metal compound no longer detectable in solution.
$^{j)}Bis(\eta^3$-methallyl)palladium.
$^{k)}$Followed by heating at 70° C. for another 24 h.
$^{l)}$13 mmol of bis(allyl)magnesium were determined in the reaction solution (IR and $^1$H-NMR spectra; protolysis).

TABLE 1a

Dehydrogenation of the ternary metal hydrides and thermal treatment of the intermetallic compounds, respectively, of the Examples 2 to 10 and results of X-ray powder analyses.

| Example No. | 1st Dehydr. or Therm. Treatm.$^{a)}$ ml of Gas$^{b)}$ | Comp. of Gases [%]$^{c)}$ | | | | | 2nd Dehydr. or Therm. Treatm.$^{a,e)}$ ml of Gas$^{b)}$ | Comp. of Gases [%]$^{c)}$ | | Composition [%]$^{f)}$ Mg M H C Empirical Formula | RP$^{g)}$ |
|---|---|---|---|---|---|---|---|---|---|---|---|
| | Amount [g] | $H_2$ | $CH_4$ | $C_2H_6$ | $C_3H_8$ | $C_4H_{10}$$^{d)}$ | Amount [g] | $H_2$ | $CH_4$ | | |
| 2 | 321 | 90 | 7 | | | 4 | | | | | $Mg_2Ni^{h)}$ (Mg) |
| 3 | 136 | 14 | 67 | 1 | 7 | 4 | 60 | 78 | 22 | 27.5 65.0 1.25 6.1 $Mg_{1.00}Ni_{1.00}H_{1.12}C_{0.46}$ | amorphous |
| 4 | 114 | 39 | 43 | — | 9 | 10 | | | | | $MgNi_3C_x$ |
| 5 | 155 | 93 | 2 | — | 3 | 2 | 108$^{k)}$ | 100 | — | | $Mg_2Pd$ j) |
| 6 | 137 | 89 | 7 | — | 3 | 2 | 96$^{k)}$ | 98 | 2 | 28.4 68.4 0.56 2.3 $Mg_{1.80}Pd_{1.00}H_{0.86}C_{0.30}$ | $Mg_2Pd$ |
| 7 | 31 | 47 | 35 | 2 | 6 | 9 | 0 | | | 17.3 74.6 0.28 1.5 $Mg_{1.00}Pd_{1.00}H_{0.39}C_{0.17}$ | amorphous |
| 8 | 87 | 80 | 3 | 1 | 9 | 8 | 0 | | | 20.1 78.5 0.50 0.4 $Mg_{2.06}Pt_{1.00}H_{1.23}C_{0.10}$ | amorphous |
| 9 | 34 | 13 | 47 | 5 | 25 | 7 | 0 | | | 11.8 86.9 0.28 0.9 $Mg_{1.10}Pt_{1.00}H_{0.62}C_{0.17}$ | amorphous |
| 10 | 144 | 96 | — | — | 4 | — | 0$^{l)}$ | | | | $MgZn_2$ |

$^{a)}$A sample of 1 to 2 g of the solid is heated in the thermovolumetric apparatus [B. Bogdanovic, B. Spliethoff, Chem.-Ing.-Techn. 55 (1983) 156] from room temperature to 400° C. at a heating rate of 1° C./min.
$^{b)}$20° C., 1 bar.
$^{c)}$According to mass-spectrometrical analysis.
$^{d)}$Result of X-ray powder analysis after the 1st dehydrogenation or thermal treatment, respectively.
$^{e)}$After the sample had been hydrogenated in an autoclave at 15 bar and 210° C. for 24 h.
$^{f)}$After the 2nd dehydrogenation or thermal treatment, respectively, according to elementary analysis.
$^{g)}$Result of X-ray powder analysis after the 2nd dehydrogenation or thermal treatment, respectively.
$^{h)}$The sample still contains 1.2% of C and 0.9% of H.
$^{i)}$E. Scheid et al Z. Metallk. 44, (1953) 387
$^{j)}$The sample shows low crystallinity. Elementary analysis: Mg 30.8, Pd 67.5, H 0.55, C 1.1%; empirical formula $Mg_{2.00}Pd_{1.00}H_{0.86}C_{0.14}$
$^{k)}$A dehydrogenation taking place at a maximum speed in a narrow temperature range is observed at 250-255° C.
$^{l)}$After the hydrogenation (10 bar, 100° C., 24 h) the sample did not evolve any gas upon heating up to 300° C.

EXAMPLE 4

In the Example, instead of $MgH_2$ there was employed the THF-soluble HMgCl (European Patent 0 003 564) with bis($n^3$-allyl)nickel in a molar ratio of 2:1. The specific surface area of the crude product was 112 m$^2$/g after drying under high vacuum and 2.2 m$^2$/g after the thermal treatment (Table 1a). In the thermal treatment (heating up to 400° C.) the amorphous product is converted into a crystalline product at 290° C. The X-ray powder diagram after the thermal treatment shows broad reflections of $MgNi_3C_x$. The sample was annealed at 660° C. for 1 h, whereupon the reflections became sharp in appearance.

| d[A]$_{exp.}$ | d$_{calc.}$ | hkl | I$_{exp.}$ |
|---|---|---|---|
| 4.102 | | | 7.1 |
| 3.824 | 3.817 | 001 | 17.3 |
| 2.204 | 2.203 | 101 | 100.0 |
| 2.108 | | | 11.0 |
| 1.908 | 1.909 | 002 | 57.7 |
| 1.708 | 1.706 | 111 | 5.7 |
| 1.490 | | | 6.9 |
| 1.349 | 1.349 | 112 | 28.7 |
| 1.151 | 1.151 | 103 | 22.0 |
| 1.102 | 1.102 | 202 | 7.1 |

EXAMPLE 5

The X-ray powder diagram after the first dehydrogenation and one further cycle of hydrogenation/dehydrogenation and after annealing at 600° C. shows sharp reflections different from those of the hexagonal compound $Mg_5 Pd_2$ ($Co_2Al_5$ type) [L. Westin, Acta Chem. Scand. 22 (1968) 2574] which reflections may be assigned to the so far unknown intermetallic phase $Mg_2Pd$ having a hexagonal lattice structure (a-6.980 Å; c-12.605 Å) as follows:

| $d[Å]_{exp.}$ | $d_{calc.}$ | hxl | $I_{exp.}$ |
|---|---|---|---|
| 3.4839 | 3.4898 | 110 | 19.9 |
| 3.1649 | 3.1515 | 004 | 44.1 |
| 2.3203 | 2.3257 | 015 | 45.3 |
| 2.2361 | 2.2481 | 121 | 100.0 |
| 2.1301 | 2.1480 | 122 | 11.9 |
| 2.0092 | 2.0145 | 030 | 11.0 |
| 1.8430 | 1.8493 | 124 | 4.2 |
| 1.8253 | 1.8166 | 033 | 16.1 |
| 1.5810 | 1.5743 | 008 | 12.3 |
| 1.5687 | 1.5733 | 035 | 7.6 |
| 1.4135 | 1.4218 | 043 | 12.3 |
| 1.3149 | 1.3191 | 140 | 10.2 |
| 1.2906 | 1.2959 | 045 | 27.1 |
| 1.2103 | 1.2147 | 235 | 7.2 |
| 1.1172 | 1.1168 | 146 | 6.4 |

The crystalline $Mg_2Pd$ reversibly reacts with $H_2$ under pressure to form the so far unknown crystalline ternary hydride $Mg_2PdH_2$ (decomposition temperature at normal pressure 250°–255° C.) which is characterized by X-ray powder analysis.

EXAMPLE 10

The amorphous hydride $MgZn_2H_2$ upon heating at 300° C. yields the known crystalline intermetallic compound $MgZn_2$ [T. Ohba et al., Acta Crystallogr. Sect. C: Cryst. Struct. Commun. (1984) C 40, 1) identified by X-ray powder analysis.

EXAMPLE 11 TO 22

Examples 11 to 22 were carried out and worked up in the same manner as in Example 1. The experimental data are set forth in Tables 2 and 2a.

TABLE 2

Reactions to metal hydrides $M^1H_n$ with bis(allyl)metal compounds ($M^2A_2$) at room temperature to give intermetallic compounds or ternary hydrides.

| Example No. | $M^1H_n$ g (mmol) | $M^2A_2$ g (mmol) | Solvent [ml] | React.-Time [h] | Propene[a] [%] | Solid [g] | Composition [%][b] $M^1$ $M^2$ H C Empirical Formula | Yield[c] [%] | RP[d] |
|---|---|---|---|---|---|---|---|---|---|
| 11 | $CaH_2$[e] 1.08 (24.4) | $PdA_2$ 2.26 (12.0) | THF (40) | 18d[f] | 64 (0.3) | 2.47 | 38.2 52.3 2.49 7.1 $Ca_{1.94}Pd_{1.00}H_{5.03}C_{1.20}$ | 100 | amorphous |
| 12 | $BaH_2$[g] 4.43 (29.9) | $NiA_2$ 2.11 (15.0) | THF (37) | 24 | 65 (4) | 5.44 | 74.7 16.0 1.6 6.7 $Ba_{2.00}Ni_{1.00}H_{5.87}C_{2.05}$ | 99 | amorphous ($BaH_2$) |
| 13 | $BaH_2$[g] 2.11 (14.3) | $NiA_2$ 2.03 (14.3) | THF (37) | 24 | 65 (3) | 2.90 | 64.2 26.5 2.1 6.7 $Ba_{1.04}Ni_{1.00}H_{5.64}C_{1.09}$ | 92 | amorphous |
| 14 | $LiH$[h] 0.26 (23.6) | $NiA_2$ (13.9) | THF (50) | 20 | 69 (2) | 1.06 | 16.0 63.5 $Li_{2.10}Ni_{1.00}$ | 83 | amorphous |
| 15 | $LiH$[h] 0.25 (23.3) | $NiA_2$ (27.4) | Toluene (44) | 216 | 63 (2) | 2.36 | 8.4 68.4 1.93 17.1 $Li_{1.04}Ni_{1.00}H_{1.64}C_{1.22}$ | 100 | amorphous |
| 16 | $LiH$[h] 0.29 (28.3) | $PdA_2$ 2.68 (14.2) | THF (50) | 60 | 51 | 1.58 | 8.5 83.7 1.91 3.4 $Li_{1.55}Pd_{1.00}H_{2.41}C_{0.36}$ | 88 | Pd |
| 17 | $LiH$[h] 0.21 (20.3) | $PtA_2$ 2.85 (10.3) | THF (50) | 24 | 60 (1) | 2.14 | | | |
| 18 | $B_2H_6$ 0.88 (31.7) | $NiA_2$ 4.04 (26.7) | Toluene (140) | 24 | — (25) | 2.05 | 21.9 63.4 2.9 10.6 $B_{1.88}Ni_{1.00}H_{2.69}C_{0.82}$ | 77 | amorphous[i] |
| 19 | $B_2H_6$ 0.54 (19.6) | $NiA_2$ 5.84 (41.5) | Toluene (90) | 60 | 18 (26) | 2.56 | 13.0 69.2 2.7 14.8 $B_{1.02}Ni_{1.00}H_{2.29}C_{1.05}$ | 73 | amorphous[j] |
| 20 | $B_2H_6$ 0.39 (14.3) | $PdA_2$ 2.23 (11.9) | THF (50) | 0.7(−15° C.) 20(−30° C.) | 72 | 1.04 | 16.3 80.0 0.73 1.7 $B_{2.00}Pd_{1.00}H_{0.96}C_{0.19}$ | 73 | |
| 21 | $SiH_4$ 1.10 (34.2) | $NiA_2$ 4.22 (30.0) | Toluene (150) | 0.5(0° C.) 72(RT) | 14 (35) | 2.76 | 24.7 45.6 4.3 21.7 $Si_{1.13}Ni_{1.00}H_{5.54}C_{2.23}$ | | amorphous |
| 22 | $SiH_4$ (14.6) | $PdA_2$ 2.75 (14.6) | THF (50) | 16(−30° C.) | 79 (16) | 1.68 | | 81 | amorphous |

[a] The figures in brackets denote % of propane.
[b] By elementary analysis.
[c] Based on initially employed $M^2$.
[d] X-ray powder analysis of the solid prior to dehydrogenation or thermal treatment, respectively.
[e] $CaH_2$ technical grade, 95%.
[f] $PdA_2$ still present in solution after 8 d.
[g] $BaH_2$ 94%.
[h] Catalytically prepared lithium hydride, % [U.S. Pat. No. 4,396,589].
[i] Specific surface area 150 m²/g.
[j] Specific surface area 164 m²/g.

TABLE 2a

Dehydrogenation of the ternary metal hydrides and thermal treatment of the intermetallic compounds, respectively, of Examples 11 to 22 and results of X-ray powder analyses.

| Example No. | 1st Dehydr. or Therm. Treatm.[a] ml of Gas[b] Comp. of Gases [%][c] | | | | | | 2nd Dehydr. or Therm. Treatm.[a,e] ml of Gas[b] Comp. of Gases [%][c] | | | Composition [%][f] $M^1$ $M^2$ H C Empirical Formula | RP[g] |
|---|---|---|---|---|---|---|---|---|---|---|---|
| | Amount [g] | $H_2$ | $CH_4$ | $C_2H_6$ | $C_3H_8$ | $C_4H_{10}$[d] | Amount [g] | $H_2$ | $CH_4$ | | |
| 11 | 43 | 6 | 88 | 37 | 2 | — h) | 44[i] | 92 | 8 | 40.1 52.4 2.06 5.0 $Ca_{2.00}Pd_{1.00}H_{4.15}C_{0.85}$ | j) |
| 12 | 45 | 39 | 54 | — | 4 | 3 $BaH_2$ | | | | | |
| 13 | 60 | 25 | 71 | — | 4 | 0.4 k) | | | | | |
| 14 | 110 | 80 | 13 | — | 3 | 1 | 16 | 86 | 14 | 15.3 70.7 1.38 5.3 $Li_{1.83}Ni_{1.00}H_{1.14}C_{0.37}$ | Ni |
| 15 | 85 | | | | | | 38 | 53 | 45 | | Ni |
| 16 | 55 | 64 | 24 | — | 6 | — | 72 | 92 | — | | l) |
| 17 | 48 | 39 | 22 | — | 6 | 3 | 65 | 100 | | 6.1 88.4 1.16 0.57 $Li_{1.92}Pt_{1.00}H_{2.54}C_{0.10}$ | |
| 18 | 149 | 11 | 67 | 5 | 15 | 2 amorphous (C 2.2, H 0.0%) | | | | | |
| 19 | 121 | 14 | 60 | 7 | 18 | 1 amorphous | | | | | |

TABLE 2a-continued

Dehydrogenation of the ternary metal hydrides and thermal treatment of the intermetallic compounds, respectively, of Examples 11 to 22 and results of X-ray powder analyses.

| Example No. | 1st Dehydr. or Therm. Treatm.[a] ml of Gas[b] Comp. of Gases [%][c] | | | | | | 2nd Dehydr. or Therm. Treatm.[a,e] ml of Gas[b] Comp. of Gases [%][c] | | | Composition [%][f] $M^1 M^2 H C$ Empirical Formula | RP[g] |
|---|---|---|---|---|---|---|---|---|---|---|---|
| | Amount [g] | $H_2$ | $CH_4$ | $C_2H_6$ | $C_3H_8$ | $C_4H_{10}$[d] | Amount [g] | $H_2$ | $CH_4$ | | |
| 20 | 0 | | | | | | | | | (C 7.1, H 1.3%) amorphous | |
| 21 | 140 | 2 | 46 | 5 | 47 | — | | | | amorphous | |
| 22 | 27 | 8 | 34 | 8 | 42 | 31 | | | | (C 2.5, H 0.6%) amorphous[m] | |

[a] A sample of 1 to 2 g of the solid is heated in the thermovolumetric apparatus [B. Bogdanovic, B. Spliethoff, Chem.-Ing.-Techn. 55 (1983) 156] from room temperature to 400° C. at a heating rate of 1° C./min.
[b] 20° C., 1 bar.
[c] According to mass-spectrometrical analysis.
[d] Result of X-ray powder analysis after the 1st dehydrogenation or thermal treatment, respectively.
[e] After the sample had been hydrogenated in an autoclave at 15 bar and 210° C. for 24 h.
[f] After the 2nd dehydrogenation or thermal treatment, respectively, according to elementary analysis.
[g] Result of X-ray powder analysis after the 2nd dehydrogenation or thermal treatment, respectively.
[h] The sample shows minor crystalline portions.
[i] In this case hydrogenation at 20° C., 13 bar, 24 h; the sample may be reversibly hydrogenated at 138° C. and dehydrogenated at 148° C.
[j] Low crystallinity; reflections at d(intensity %) 2.2480(100), 2.4099(40), 1.4953(40), 2.8126(36), 2.0095(36).
[k] Very broad reflections, attributable to $BaH_2$ and Ni; C 1.2, H 0.8%.
[l] Reflections at d(intensity %) 2.280(100), 1.985(20), 2.776(27), 3.809(18), 3.887(17).
[m] The sample cannot be hydrogenated under standard conditions. Elementary analysis: Si 17.0, Pd 79.0, H 0.32, C 3.63%; empirical formula $Si_{1.00}Pd_{1.22}H_{0.51}C_{0.50}$.

EXAMPLE 16

The amorphous intermetallic compound $Li_{1.5}Pd$, after heating at 400° C. and one cycle of hydrogenation/dehydrogenation shows broad reflections in the X-ray diagram (cf. Table 2a). LiPd in a crystalline form has been known (cubic crystal lattice, $CeCl$ type) [J. H. N. Van Vucht, K. H. J. Buschow, J. Less-Common Metals 48, (1976) 345; O. Loebich, Ch. J. Raub, J. Less-Common Metals 55 (1977) 67].

EXAMPLE 17

The amorphous intermetallic compound $Li_2Pt$ under standard conditions reversibly reacts with hydrogen (Table 2a). The crystalline Laves phase $Li_2Pt$ has been known [W. Bronger et al., J. Less-Common Metals 43, (1975) 143; O. Loebich, Ch. J. Raub, J. Less-Common Metals 70 (1980) 47].

EXAMPLE 23

To a solution of 2.19 g (26.6 mmol) of $Mg(C_2H_5)_2$ in 40 ml of THF there is dropwise added at room temperature with stirring within 1 h a solution of 2.56 g (13.6 mmol) of $Pd(\eta-C_3H_5)_2$ in 20 ml of THF. Already upon the addition of the first drops a black precipitate was formed and gas evolution began. The gas evolved during the reaction (4 h) was collected in a gas burette connected to the reaction vessel. According to analysis by mass spectrometry, 29.9% of $C_2H_4$, 17.4% of $C_2H_6$ and 12.9% of $C_3H_6$, each relative to the calculated amounts, were released.

The batch was stirred at room temperature for another 22 h. Then the volatiles were evaporated at 0.27 mbar (0.2 mmHg) and condensed in two cold traps arranged in series (−78° C. and −196° C.). The gases condensed in the trap cooled at −196° C. were evaporated, collected in a gas burette and analyzed by mass spectroscopy; there were detected 12.2% of $C_2H_4$, 4.8% of $C_2H_6$ and 36.8% of $C_3H_6$, each relative to the calculated amounts. The distillation residue was stirred with 40 ml of fresh THF, the solid was separated from the solution by filtration, washed with THF until colorless and then dried under high vacuum.

There were obtained 1.92 g of a black, highly pyrophoric solid having the composition Mg 18.8, Pd 78.2, H 0.68, C 2.5, conforming to an empirical formula of $MgPdH_{0.92}C_{0.29}$ (98% based on Pd). According to the X-ray powder analysis, the solid was amorphous.

In the thermal treatment (up to 400° C., 1° C./min), 1.05 g of the solid produced 25 ml of gas (20° C., 1 bar) having the composition: $H_2$ 15.2, $CH_4$ 9.1, $C_3H_8$ 96.4, $C_4H_{10}$ 36.4%. After a pressure hydrogenation (25 bar of $H_2$, 250° C., 24 h), the sample of the solid was again subjected to the programmed temperature-controlled thermolysis as above; no evolution of gas occurred, and the sample due to its X-ray powder diagram was amorphous. The mother liquor obtained upon the recovery of the solid upon hydrolysis gave 24.7% of $C_2H_6$ and 30.5% of $C_3H_6$, relative to the respective calculated amounts, and the aqueous phase contained 12.5 mmol or $Mg^{2+}$ (45% of the starting amount) and 0.34 mmol of $Pd^{2+}$ (2.5% of the calculated amount). Due to the gases evolved in the reaction and upon hydrolysis and to the analysis of the solid and of the solution, the reaction of $Mg(C_2H_5)_2$ with $Pd(\eta-C_3H_5)_2$ may be described by the reaction equation (4) as set forth hereinabove.

APPLICATION EXAMPLE 1

[Use of the amorphous intermetallic hydride $Mg_2PdH_2$ (Example 5) as a catalyst for the selective hydrogenation of hexyne-3 to form cis-hexane-3].

0.25 g (7.6 mmol) of the active magnesium hydride prepared according to the European Patent No. 0 003 564 Cr cat., 20° C.) in 5 ml of toluene were admixed with a solution of 0.53 mg (0.003 mmol) of $Pd(\eta^3-C_3H_5)_2$ in 4 ml of toluene, and the suspension was stirred for 0.5 h. After 20 h of stirring under a hydrogen atmosphere (1 bar of hydrogen, 20° C.) 3.8 ml (34 mmol) of hexyne-3 were added (molar ratio of Pd:hexyne-3-1:23000), whereupon an immediate hydrogen consumption began to occur. Until completion of the reaction 790 ml of $H_2$ (1 bar, 20° C.) were taken up (99% of the theoretical amount) in the course of 1 h 40 min.

According to the gas-chromatographic analysis the product had the following composition: cis-hexane-3 96%, trans-hexane-3 2%, trans-hexane-2 0.4%, cis hexane-2 0.4%, n-hexane 1%.

APPLICATION EXAMPLES 2 TO 8

[Use of the amorphous intermetallic nickel compounds as hydrogenation catalysts]

The amorphous intermetallic nickel compounds $Mg_2NiH_2$ (Example 1), $NiBC_xH_y$ (Example 19), $NiB_2C_xH_y$ (Example 16), $NiSiC_xH_y$ (Example 21), $MgNiC_x$ (Example 3), BaNi (Example 13) and the crystalline compound $Mg_2NiH_4$ (after 34 cycles of hydrogenation/dehydrogenation, Example 1), were used as hydrogenation catalysts for the hydrogenation of a mixture of cyclohexane and heptane-1 in a molar ratio of 10:7 (molar ratio Ni:alkene-1:40) and compared to a conventional Raney nickel catalyst.

In FIG. 1, the respective hydrogen consumption rates are plotted over the period of reaction.

$Mg_2NiH_2$ has proven to be the best hydrogenation catalyst having an activity of about 12 times that of Raney Ni. Both $NiB_2C_xH_y$ and $NiBC_xH_y$ are still 6 times as active as Raney Ni is under comparable conditions. Particularly conspicuous are the very large surface areas of 149.9 $m^2/g$ and 164.0 $m^2/g$, respectively, of the boron compounds which are supposed to contribute to the high activities of the catalysts.

The activity of $NiSiC_xH_y$ is nearly identical to that of $NiBC_xH_y$. Even the BaNi, in spite of its low surface area, shows considerable activity exceeding that of Raney Ni by a factor of 1.4.

It will be understood that the specification and examples are illustrative but not limitative of the present invention and that other embodiments within the spirit and scope of the invention will suggest themselves to those skilled in the art.

What is claimed is:

1. An intermetallic compound selected from the group consisting of
   a) crystalline $Mg_2Pd$,
   b) amorphous MgPd,
   c) $Mg_2Pt$,
   d) MgPt,
   e) $Li_2Ni$
   f) LiNi,
   g) BaNi,
   h) $Ba_2Ni$,
   i) amorphous LiPd,
   j) amorphous $Li_2Pt$,
   k) $Ca_2Pd$, and 2. A compound according to claim 1, wherein such compound is crystalline $Mg_2Pd$.

3. A compound according to claim 1, wherein such compound is amorphous MgPd.

4. A compound according to claim 1, wherein such compound is $Mg_2Pt$.

5. A compound according to claim 1, wherein such compound is MgPt.

6. A compound according to claim 1, wherein such compound is $Li_2Ni$.

7. A compound according to claim 1, wherein such compound is LiNi.

8. A compound according to claim 1, wherein such compound is BaNi.

9. A compound according to claim 1, wherein such compound is $Ba_2Ni$.

10. A compound according to claim 1, wherein such compound is amorphous LiPd.

11. A compound according to claim 1, wherein such compound is amorphous $Li_2Pt$.

12. A compound according to claim 1, wherein such compound is $Ca_2Pd$.